United States Statutory Invention Registration [19]

[11] Reg. Number: H138

Gilbert [43] Published: Oct. 7, 1986

[54] SOLID POLY(AZIDOMETHYL)BENZENE EXPLOSIVE COMPOSITION

[75] Inventor: Everett E. Gilbert, Morristown, N.J.

[73] Assignee: The United States of America as represented by the Secretary of the Army, Washington, D.C.

[21] Appl. No.: 655,609

[22] Filed: Sep. 28, 1984

[51] Int. Cl.[4] ..... C07C 107/04
[52] U.S. Cl. ..... 260/349; 149/109.4
[58] Field of Search ..... 260/349

[56] References Cited

PUBLICATIONS

Sommers, et al.; J.A.C.S., 79, (1957), pp. 3491–3492.
McGrath; C.A., 74: 142858n (1971).

*Primary Examiner*—Richard D. Lovering
*Assistant Examiner*—Jack Thomas
*Attorney, Agent, or Firm*—Anthony T. Lane; Robert P. Gibson; Edward F. Costigan

[57] ABSTRACT

Poly(azidomethyl)benzenes having the formula $$C_6H_{6-N}(CH_2N_3)_N$$

wherein n represents 3 to 6 inclusive. These compounds are for use as novel explosives.

4 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

SOLID POLY(AZIDOMETHYL)BENZENE EXPLOSIVE COMPOSITION

GOVERNMENTAL INTEREST

The invention described herein may be manufactured, used and licensed by or for the Government for Governmental purposes without payment to me of any royalties thereon.

In general, this invention relates to poly(azidomethyl)benzenes for use as an explosive.

More particularly, this invention relates to poly(azidomethyl)benzenes having the formula:

$$C_6H_{6-N}(CH_2N_3)_n$$

wherein n represents 3 to 6 inclusive which may be used as an explosive.

BACKGROUND OF INVENTION

Azidomethyl derivatives of benzene are known; they include 1,4-bis (azidomethyl) benzene (Jour. Amer. Chem. Soc. 79,3491 (1957)) and monoazidomethylbenzene (Encyc. of Explosives and Related Items, Vol. 2, pg. B94). However, due to their physical properties, they have not proved of practical interest as explosives.

SUMMARY OF INVENTION AND DETAILED DESCRIPTION

The novel explosive compounds of this invention are prepared by heating a poly(halomethyl)benzene with a metallic azide according to the equation:

$$C_6H_{6-N}(CH_2X)_N + MeN_3 \rightarrow C_6H_{6-N}(CH_2N_3)_N$$

wherein X is a halogen, usually chlorine or bromine, Me is a metal, and n represents 3 to 6 inclusive. The organic solvents which may be used as the reaction medium include ethanol, acetone, ethylene glycol monoethyl ether, dimethyl sulfoxide, dimethyl formamide, and N-methyl pyrrolidinone.

EXAMPLES OF PREPARATION

1. Preparation of hexakis (azidomethyl) benzene.

18.0 g. (0.028 mole) of hexakis (bromomethyl) benzene (prepared in accordance with the Jour. Am. Chem. Soc. 100,2173 (1978) and 15.0 9. (0.23 mole) of sodium azide were reacted in 75 ml of dimethylformamide by mixing at 75°–80° C. for 1 hour. The reaction mixture was cooled and poured into cold water to precipitate the white solid product which was filtered, washed and dried. The yield was 11.5 g. which is 100 percent of theory. The product melted with decomposition at 163° C., and again at the same temperature after recrystallization from dioxane and water.

The identity of the product as hexakis (azidomethyl) benzene was proven by infra-red spectrum, NMR spectral analysis, and elemental analysis for C, H, and N.

Upon heating, a pinch of the material melted on a spatula, and shortly thereafter detonated sharply.

2. Preparation of hexakis (azidomethyl) benzene.

0.5 g. of hexakis (bromomethyl) benzene, 0.4 g. of sodium azide, and 15 ml. of dimethylformamide were mixed by stirring at room temperature for 2 hours. The reaction mixture was poured into water, the solid was filtered, and washed with water and methanol. The yield of product was 0.3 g. which was 100 percent of theory.

The product was proven to be hexakis (azidomethyl) benzene by melting point and infra-red spectrum.

3. Preparation of 1,3,5-tris (azidomethyl) benzene.

1.3 g. (0.0034 mole) of 1,3,5-tris (bromomethyl) benzene (prepared according to Chem. Ber. 106,717 (1973), and 0.8 g. (0.12 mole) of sodium azide were mixed in 15 ml. of dimethylformamide for 5 hours at 75° C. The reaction mixture was poured into water, and an oil separated which was extracted with methylene chloride. The solvent was removed and 0.7 g. of the product, a colorless oil was obtained, which was 86 percent of theory.

The above product was identified as 1,3,5-tris (azidomethyl) benzene by infra-red spectrum.

A drop of the product was placed in a test-tube, and heated over a low Bunsen flame at which time it detonated with a loud report.

4. Preparation of 1,2,4,5-tetrakis (azidomethyl) benzene.

0.9 g. (0.002 mole) of 1,2,4,5-tetrakis (bromomethyl) benzene (prepared in accordance with J. Het. Chem. 983, (1973), and 1.0 g. (0.015 mole) of sodium azide were mixed with stirring in 25 ml. of dimethylformamide for 1 hour at 80° C. The reaction mixture was poured into water, and the solids were filtered and dried. The product yield was 0.6 g. which was 100 percent of theory. The melting point of the solid product was 50° C. It was identified as 1,2,4,5-tetrakis (azidomethyl) benzene by infra-red spectrum. The latter compound detonated upon heating above its melting point.

5. Preparation of 1,3,5-tris(azidomethyl) -2,4,6-trimethylbenzene.

1.0 g. of 1,3,5-tris (bromomethyl) -2,4,6-trimethylbenzene and 0.70. of sodium azide were mixed in 25 ml. of dimethylformamide for 1 hour at 75° C. The reaction mixture was poured into water, and the solid product was filtered. The yield of product was 0.6 g. which was 85 percent of theory. The product melted at 60° C. upon recrystallization from methylcyclohexane. The product was identified by infra-red spectrum. Upon heating above its melting point, the product flashed.

RESULTS

In general, hexakis (azidomethyl) benzene has been found to be a white solid melting at 165° C., which can be prepared from inexpensive raw material. It contains nearly 62 percent azide nitrogen. It is more sensitive to impact than lead azide or styphnate, but less sensitive to friction or electric charge. It is stable to heat when tested by the Vacuum Stability Test, and stable to aqueous hydrolysis. It is suitable for use as a hot-wire initiator but is less sensitive than lead styphnate. The compound has been subjected to the mandatory tests required for qualification as an explosive.

More particularly, the cited hexakis (azidomethyl) benzene melts in a capillary at 162°–5° C. with gas evolution and darkening. On rapid heating on a spatula, the compound melts and shortly thereafter detonates. It is insoluble in water, and does not undergo any change upon heating in water for one week at 60° C. It is poorly soluble in organic solvents but maybe recrystallized from tetrahydrofuran or toluene. It has been found to undergo surface darkening upon prolonged exposure to light.

Specifically, the cited hexakis (azidomethyl) benzene is comparatively stable thermally. Its Auto-ignition Temperature is 173° C. which is in the area of Composition B (174° C.). The Five Second Explosive Temperature of 255° C. was determined bny the closed-cup procedure. It has practically the same response as nitroguanidine. The Explosion Temperature Test was ran with 20 mg. of explosive. At this lower dosage, the cited compound showed more disruption of the blasting cap, and more splashing of the Woods metal than 40 mg. of RDX.

Further, the cited hexakis compound has a substantially lower electrostatic and friction sensitivity than other primary explosives. In the Hot-Wire Initiation Test, the substantially high voltage required is regarded as a safety factor.

In summary, the cited hexakis compound is insoluble in water, stable to hydrolysis, and poorly soluble in organic solvents. It has a density of 1.392 g/cc, explodes in concentrated sulfuric acid, and gradually darkens in light. It passed the Vacuum Stability Test for 40 hours at 100° C., the Five Second Explosion Temperature is 255° C. The activation energy is 30.8 K cal/mole and the Auto-ignition Temperature is 173°.

In conclusion note should be also be taken that the isomers 1,2,3 and 1,2,4 of tris (azidomethyl) benzene, and the isomers 1,2,3,4 and 1,2,3,5 of tetrakis (azidomethyl) benzene may be similarly prepared from the known bromomethyl or chloromethyl analogues.

The foregoing disclosure is merely illustrative of the principles of this invention and is not to be interpreted in a limiting sense. I wish it to be understood that I do not desire to be limited to the exact details of construction shown and described because obvious modifications will occur to a person skilled in the art.

What is claimed is:

1. A solid explosive selected from the group consisting of:

a. Hexakis (azidomethyl) benzene, b. 1,3,5-Tris (azidomethyl) benzene, c. 1,2,4,5-Tetrakis (azidomethyl) benzene.

2. The solid explosive of claim 1 being Hexakis (azidomethyl) benzene.

3. The solid explosive of claim 1 being 1,3,5-Tris (azidomethyl) benzene.

4. The solid explosive of claim 1 being 1,2,4,5-Tetrakis (azidomethyl) benzene.

* * * * *